(12) United States Patent
Kim et al.

(10) Patent No.: US 10,208,185 B2
(45) Date of Patent: Feb. 19, 2019

(54) ESTER-BASED COMPOUND, PLASTICIZER COMPOSITION INCLUDING THE SAME, PREPARATION METHOD OF THE COMPOSITION AND RESIN COMPOSITION INCLUDING THE PLASTICIZER COMPOSITION

(71) Applicant: LG CHEM, LTD., Seoul (KR)

(72) Inventors: Hyun Kyu Kim, Daejeon (KR); Mi Yeon Lee, Daejeon (KR); Jeong Ju Moon, Daejeon (KR); Joo Ho Kim, Daejeon (KR); Seok Ho Jeong, Daejeon (KR)

(73) Assignee: LG Chem, Ltd., Seoul (KR)

( * ) Notice: Subject to any disclaimer, the term of this patent is extended or adjusted under 35 U.S.C. 154(b) by 163 days.

(21) Appl. No.: 15/038,989

(22) PCT Filed: Feb. 5, 2015

(86) PCT No.: PCT/KR2015/001202
§ 371 (c)(1),
(2) Date: May 24, 2016

(87) PCT Pub. No.: WO2015/119442
PCT Pub. Date: Aug. 13, 2015

(65) Prior Publication Data
US 2017/0166724 A1 Jun. 15, 2017

(30) Foreign Application Priority Data

| | | | |
|---|---|---|---|
| Feb. 7, 2014 | (KR) | ......................... | 10-2014-0014203 |
| Feb. 24, 2014 | (KR) | ......................... | 10-2014-0021409 |
| Feb. 24, 2014 | (KR) | ......................... | 10-2014-0021593 |
| Feb. 24, 2014 | (KR) | ......................... | 10-2014-0021597 |
| Feb. 24, 2014 | (KR) | ......................... | 10-2014-0021598 |
| Feb. 4, 2015 | (KR) | ......................... | 10-2015-0017573 |
| Feb. 4, 2015 | (KR) | ......................... | 10-2015-0017574 |
| Feb. 4, 2015 | (KR) | ......................... | 10-2015-0017575 |
| Feb. 4, 2015 | (KR) | ......................... | 10-2015-0017576 |
| Feb. 4, 2015 | (KR) | ......................... | 10-2015-0017577 |

(51) Int. Cl.
| | |
|---|---|
| C08K 5/00 | (2006.01) |
| C08K 5/12 | (2006.01) |
| C07C 67/08 | (2006.01) |
| C07C 69/80 | (2006.01) |
| C08L 27/06 | (2006.01) |

(52) U.S. Cl.
CPC ............ C08K 5/12 (2013.01); C07C 67/08 (2013.01); C07C 69/80 (2013.01); C08L 27/06 (2013.01); C08K 5/0016 (2013.01)

(58) Field of Classification Search
CPC ........... C07C 67/08; C07C 69/80; C08K 5/12; C08K 5/0016; C08L 27/06

USPC ........................................................ 524/297
See application file for complete search history.

(56) References Cited

U.S. PATENT DOCUMENTS

| | | | |
|---|---|---|---|
| 3,096,364 A | 7/1963 | Gamrath et al. |
| 3,324,040 A | 6/1967 | Spoor |
| 3,736,348 A | 5/1973 | Gough et al. |
| 4,395,496 A | 7/1983 | Wittmann et al. |
| 4,929,749 A | 5/1990 | Gupta et al. |
| 7,208,545 B1 | 4/2007 | Brunner et al. |
| 2008/0234414 A1 | 9/2008 | Godwin et al. |
| 2010/0048778 A1 | 2/2010 | Godwin et al. |
| 2010/0130394 A1 | 5/2010 | Tsubouchi |

FOREIGN PATENT DOCUMENTS

| | | |
|---|---|---|
| CN | 101668835 A | 3/2010 |
| CN | 102604155 A | 7/2012 |
| GB | 851753 A | 10/1960 |
| GB | 904340 A | 8/1962 |
| GB | 1456598 A | 11/1976 |
| JP | 49-81449 | 8/1974 |
| JP | 50-83443 A | 7/1975 |
| JP | 61-243845 A | 10/1986 |
| JP | 05-295206 A | 11/1993 |
| JP | 05-295207 A | 11/1993 |

(Continued)

OTHER PUBLICATIONS

Burkhard, Charles A., Burnett, Robert E., "Hydrolysis of Diethyl Methoxyphthalates," Journal of the American Chemical Society, vol. 80, p. 341-343, Jan. 20, 1958.

(Continued)

Primary Examiner — Angela C Scott
(74) Attorney, Agent, or Firm — Dentons US LLP

(57) ABSTRACT

The present invention provides an ester compound of the following Formula 1, a plasticizer composition including the same and a resin composition including the plasticizer composition.

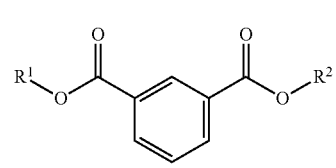

<Formula 1>

In the above formula, $R^1$ and $R^2$ are different from each other and are independently at least one selected from the group consisting of $C_3$-$C_{10}$ alkyl of a non-branch type or including at least one branched chain, a substituted or unsubstituted alkyl aryl and a substituted or unsubstituted aryl. When the novel ester compound according to an embodiment of the present invention is used in a resin composition, eco-friendly property and good physical properties including plasticizing efficiency, tensile strength, elongation rate, migration loss, volatility resistance, etc. may be provided.

9 Claims, No Drawings

(56) References Cited

FOREIGN PATENT DOCUMENTS

| | | |
|---|---|---|
| JP | 07-157614 A | 6/1995 |
| JP | 2001-031794 A | 2/2001 |
| JP | 2003-502399 A | 1/2003 |
| JP | 2012-89287 A | 5/2012 |
| JP | 2012-255104 A | 12/2012 |
| KR | 2013-0035493 A | 4/2013 |
| RU | 2401847 C2 | 10/2010 |
| TW | 375563 | 12/1999 |
| WO | 2013/143881 A1 | 10/2013 |

OTHER PUBLICATIONS

Office Action of Korean Patent Office in Appl'n No. 10-2015-0017581, dated Aug. 31, 2017.

ESTER-BASED COMPOUND, PLASTICIZER COMPOSITION INCLUDING THE SAME, PREPARATION METHOD OF THE COMPOSITION AND RESIN COMPOSITION INCLUDING THE PLASTICIZER COMPOSITION

This application is the National Phase Entry of PCT/KR2015/001202 filed on Feb. 5, 2015 and claims the benefit of Korean Patent Application Nos. 10-2014-0014203 filed Feb. 7, 2014, 10-2014-0021409, 10-2014-0021593, 10-2014-0021597 and 10-2014-0021598 all filed Feb. 24, 2014, 10-2015-0017573, 10-2015-0017574, 10-2015-0017575, 10-2015-0017576, 10-2015-0017577 all filed Feb. 4, 2015 in the Korean Intellectual Property Office, the disclosures of which are herein incorporated by reference in their entirety.

TECHNICAL FIELD

The present invention relates to an isophthalate-based ester compound, a plasticizer composition including the same, a preparation method of the plasticizer composition and a resin composition including the plasticizer composition.

BACKGROUND ART

Polymer resins are used in diverse fields such as daily supplies, home electronic appliances, clothes, vehicles, construction materials or packing materials, etc. in accordance with each characteristic.

Until now, plastic resins such as polyethylene (PE), polypropylene (PP), polystyrene (PS), polyurethane (PU), polyvinyl chloride (PVC), etc. are widely used. Particularly, since a PVC resin has hard and soft properties, is capable of being molded in diverse shapes, has good price competitiveness, and so has a wide range of usability, the PVC resin is applied in diverse application fields from the daily supplies to the construction materials.

The PVC resin is used with a plasticizer to realize diverse physical properties rather than used solely. The PVC resin is imparted with flexibility by the plasticizer, thereby improving processability and applicability thereof. However, as the industry advances, the role of the plasticizer becomes diverse, and properties required in applied fields become diverse including volatility resistance, migration resistance, ageing resistance, cold resistance, oil resistance, water resistance, heat resistance, etc., other than the flexibility.

As the ester compound used as the plasticizer recently, di-(2-ethylhexyl) phthalate (DEHP), diisononyl phthalate (DINP), di-2-propylheptyl phthalate (DPHP), diisodecyl phthalate (DIDP), etc. are widely used. However, these compounds are environmental hormones disturbing endocrine system and are harmful to a human body, and have a limit in improving the processability of a resin, absorption rate with a resin, volatile loss, the degree of migration loss and heat stability.

Thus, the development on an ester compound which is eco-friendly, sufficiently improves all physical properties including the processability of a resin, the absorption rate with a resin, hardness, tensile strength, elongation rate, volatile loss, the degree of migration loss, heat stability, etc., and a method of preparing the same is required.

DISCLOSURE OF THE INVENTION

Technical Problem

The first technical task intend to solve in the present invention is a novel compound for a plasticizer, and the present invention provides a novel ester compound for a plasticizer which is eco-friendly and improves absorption rate with respect to a resin and the processability of a resin with short melting time when used in a resin composition, thereby providing good physical properties such as tensile strength, elongation rate, migration resistance, volatility resistance, etc.

The second technical task intend to solve in the present invention is to provide a plasticizer composition including the ester compound.

The third technical task intend to solve in the present invention is to provide a preparation method of the plasticizer composition.

The fourth technical task intend to solve in the present invention is to provide a resin composition including the ester compound.

Technical Solution

According to an aspect of the present invention, there is provided an ester compound of the following Formula 1.

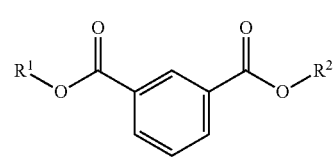

<Formula 1>

In the above formula, $R^1$ and $R^2$ are different from each other and are independently at least one selected from the group consisting of $C_3$-$C_{10}$ alkyl of a non-branch type or including at least one branched chain, a substituted or unsubstituted alkyl aryl and a substituted or unsubstituted aryl.

In addition, there is provided in the present invention a plasticizer composition including the ester compound of the above Formula 1.

In addition, there is provided in the present invention a preparation method of the plasticizer composition including conducting an esterification reaction of isophthalic acid of the following Formula 2 with at least one alcohol of the following Formula 3 or a mixture of the alcohol with at least one isomer thereof in the presence of a catalyst.

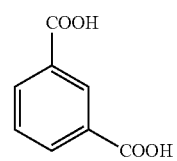

<Formula 2>

R'OH  <Formula 3>

In the above formula, R' is at least one selected from the group consisting of a $C_3$-$C_{10}$ alkyl of a non-branch type or including at least one branched chain, a substituted or unsubstituted alkyl aryl and a substituted or unsubstituted aryl.

Also, in an embodiment of the present invention, there is provided a polyvinyl chloride resin composition including the plasticizer composition.

Further, in an embodiment of the present invention, there is provided a resin composition including the plasticizer composition.

Advantageous Effects

The ester compound according to an embodiment of the present invention is a novel isophthalate-based ester compound for a plasticizer, and when used in a resin composition, plasticization efficiency is good and good physical properties such as tensile strength, elongation rate, migration resistance, volatility resistance, etc. may be provided.

MODE FOR CARRYING OUT THE INVENTION

Hereinafter, the present invention will be explained in detail to assist the understanding of the present invention.

It will be understood that terms or words used in the present disclosure and claims should not be interpreted as having a meaning that is defined in common or in dictionaries, however should be interpreted in consistent with the technical scope of the present invention on the basis of the principle that inventors may appropriately define the concept of the terms to explain the invention at his best method.

The term "hybrid type" used in the present invention refers to a structure having different substituted alkyl groups at symmetric positions of a phenyl group if not specifically defined.

In addition, the term "non-hybrid type" used in the present invention refers to a structure having the same substituted alkyl groups at symmetric positions of a phenyl group if not specifically defined.

According to an embodiment of the present invention, an ester compound of the following Formula 1 is provided.

<Formula 1>

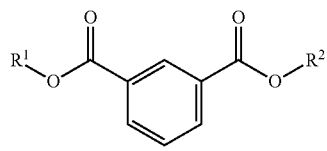

In the above formula, $R^1$ and $R^2$ are different from each other and are independently at least one selected from the group consisting of $C_3$-$C_{10}$ alkyl of a non-branch type or including at least one branched chain, a substituted or unsubstituted alkyl aryl and a substituted or unsubstituted aryl.

In this case, the branched chain may be $C_1$-$C_6$ alkyl, $C_2$-$C_6$ alkenyl or $C_2$-$C_6$ alkynyl.

The ester compound of the above Formula 1 according to an embodiment of the present invention may preferably be an ester compound where $R^1$ and $R^2$ are different from each other and are independently at least one selected from the group consisting of $C_4$-$C_9$ alkyl of a non-branch type or including at least one branched chain of $C_1$-$C_4$ alkyl, and phenyl or benzyl of a non-branch type or including at least one branched chain of $C_1$-$C_4$ alkyl.

The ester compound of the above Formula 1 according to an embodiment of the present invention may more preferably be at least one ester compound selected from compounds in the following formulae.

<Formula 1-1>

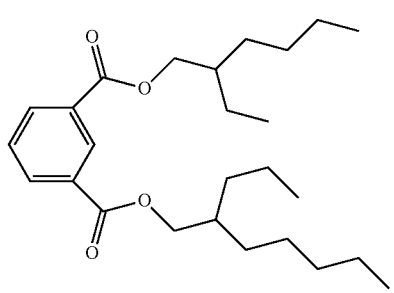

<Formula 1-2>

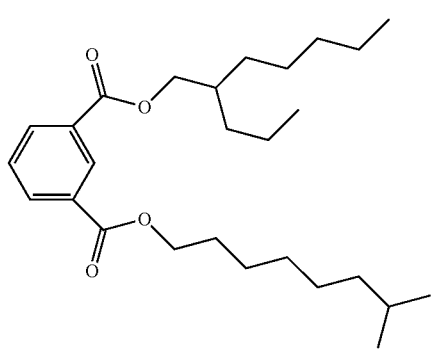

<Formula 1-3>

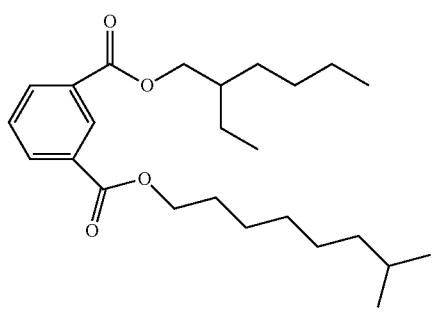

<Formula 1-4>

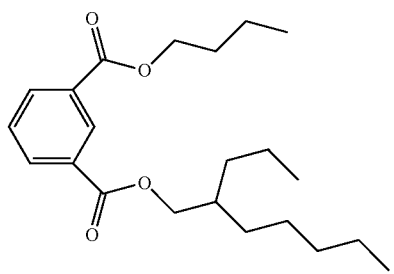

<Formula 1-5>
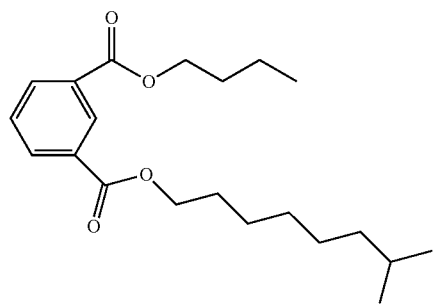
<Formula 1-6>
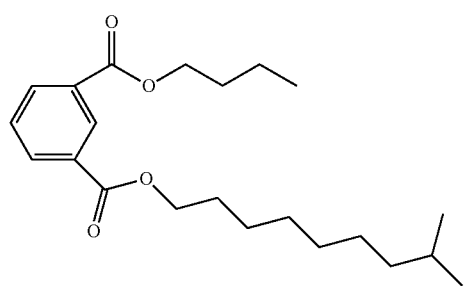
<Formula 1-7>
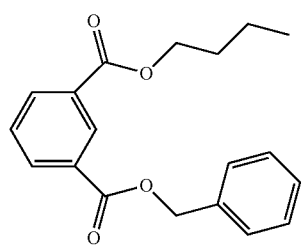
<Formula 1-8>
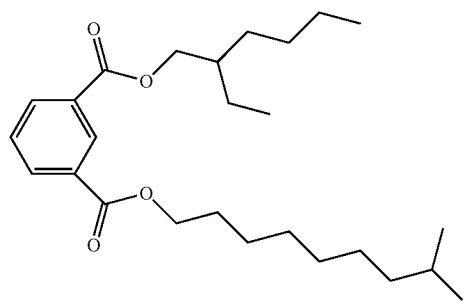
<Formula 1-9>
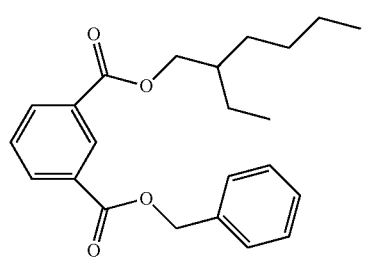
<Formula 1-10>
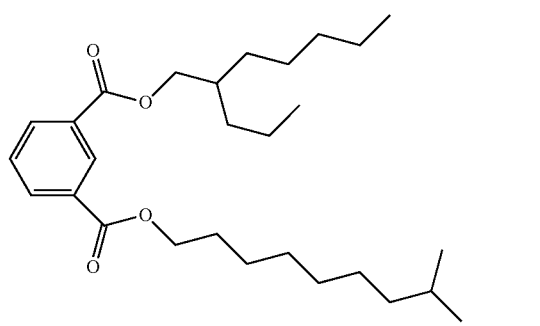
<Formula 1-11>
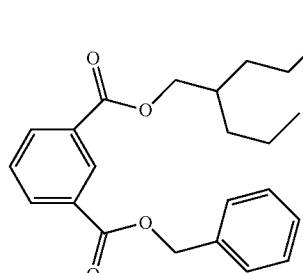
<Formula 1-12>
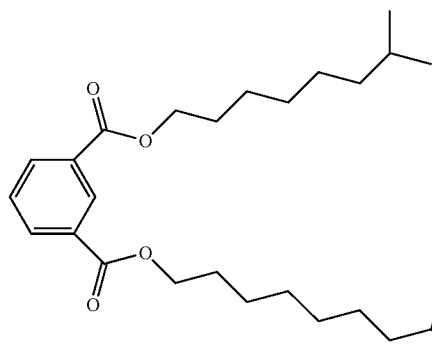
<Formula 1-13>
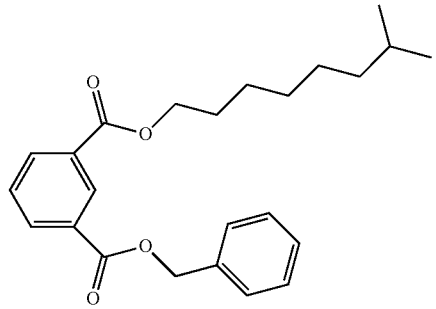
<Formula 1-14>
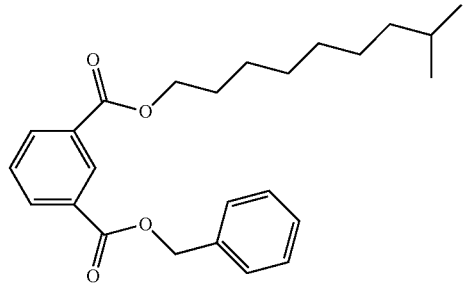

-continued

<Formula 1-15>

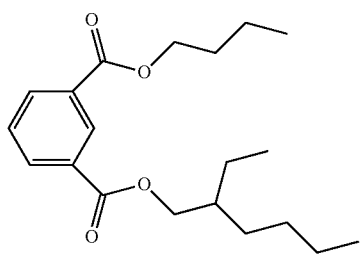

<Formula 1-16>

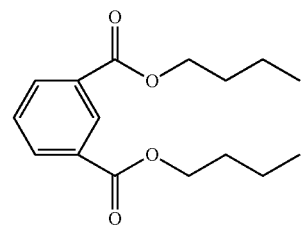

<Formula 1-17>

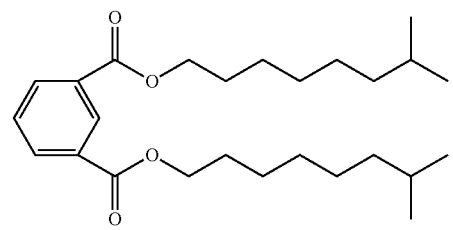

<Formula 1-18>

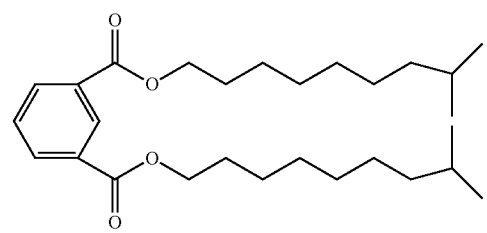

<Formula 1-19>

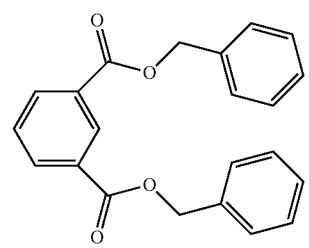

<Formula 1-20>

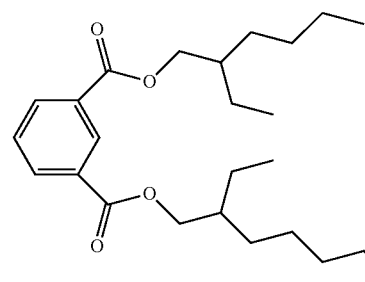

<Formula 1-21>

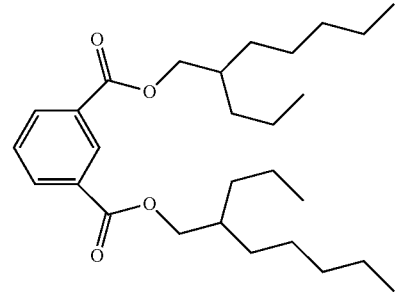

The hybrid type ester compound according to an embodiment of the present invention is a novel compound for a plasticizer and has high purity, low amount of residual alcohol and low water content. In the case of using in a resin composition, eco-friendly characteristics, improved processability of the resin due to short absorption rate and short melting time with respect to a resin, and good physical properties may be provided.

The ester compound according to an embodiment of the present invention is an isophthalate-based ester compound in which ester groups (—COO—) are present at positions 1 and 3 in a benzene ring, that is, at a meta position, and is more eco-friendly and has better physical properties including tensile strength, elongation rate, migration resistance, volatility resistance, etc. when compared to a phthalate-based ester compound having ester groups (—COO—) at other positions, for example an ortho position (positions 1 and 2 in a benzene ring) or a para position (positions 1 and 4 in a benzene ring).

Particularly, benzenedicarboxylic acid of an ortho position used as a raw material for preparing a phthalate-based ester compound having ester groups at the ortho position has a limit and is not free from a phthalate issue, particularly defects of environmental contamination and harmfulness to a human body. Meanwhile, the phthalate-based ester compound having ester groups at para position has relatively deteriorated compatibility and combination stability with the resin due to the linear structure thereof, and these defects may be adversely affecting factors to the processability and workability of a product.

In the case of using the ester compound according to an embodiment of the present invention as the plasticizer of the resin composition, equivalent tensile strength and elongation rate may be secured when compared to a phthalate-based compound widely used as a common plasticizer. Particularly, migration loss (%) and volatile loss (%) are markedly decreased by ½ and over than DIDP, and such decrease may mean the decrease of the amount of an ester compound (plasticizer) present in a specimen. In other words, equal to or better overall physical properties than a common phthalate-based ester compound may be realized.

The present invention may provide a plasticizer composition further including at least one compound selected from the group consisting of the compounds of the following formulae according to an embodiment.

Here, the non-hybrid type plasticizer compound as in the above Formulae 1-16 to 21 may be included in a final product when conducting an esterification reaction of the hybrid type compound. Particularly, the plasticizer composition may have a configuration including one of the compounds of Formulae 1-1 to 1-15 as a hybrid type isophthalate compound and at least two selected from the group consisting of the compounds of Formulae 1-16 to 21 as a non-hybrid type isophthalate compound.

The total amount of the hybrid type isophthalate compound and the non-hybrid type isophthalate compound of the plasticizer composition may be from 5 to 80 wt % of the hybrid type isophthalate compound and from 20 to 95 wt % of the total non-hybrid type isophthalate compounds on the basis of the total amount of the plasticizer composition. Preferably, from 10 to 60 wt % of the hybrid type isophthalate compound and from 40 to 90 wt % of the total non-hybrid type isophthalate compounds may be included. In the case that the amount of the hybrid type isophthalate-based compound is less than 5 wt % in the total amount of the plasticizer composition, the improvement of physical properties such as hardness, tensile strength, elongation rate, viscosity stability, etc. may be insignificant, and in the case that the hybrid type isophthalate-based compound exceeds 80 wt % in the total amount of the plasticizer composition, migration resistance, volatile loss and processability may be deteriorated.

According to another embodiment of the present invention, a plasticizer composition including compounds of the following formulae may be provided.

<Formula 1-1>

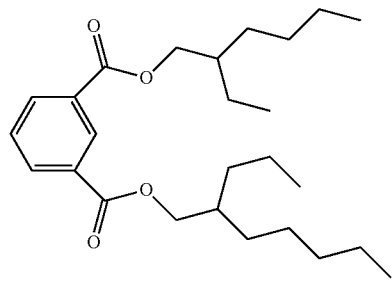

<Formula 1-20>

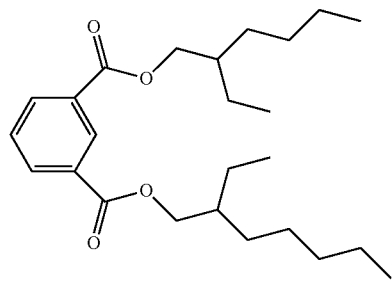

and

<Formula 1-21>

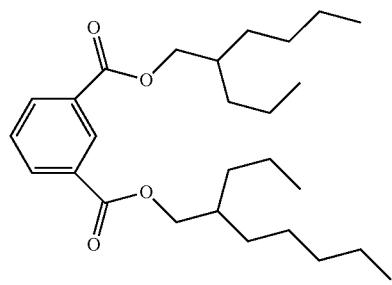

In addition, the plasticizer composition may include the compounds of the following formulae.

<Formula 1-2>

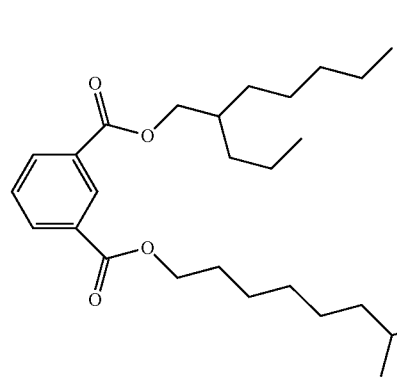

<Formula 1-17>

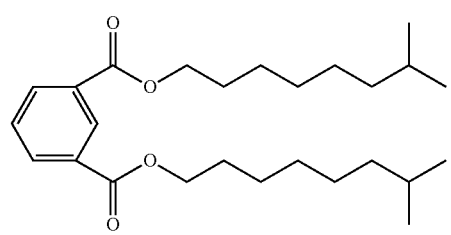

and

<Formula 1-21>

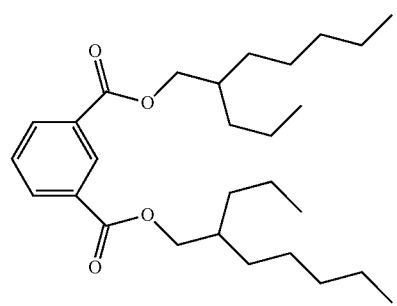

Alternatively, the compounds of the following formulae may be included.

<Formula 1-3>

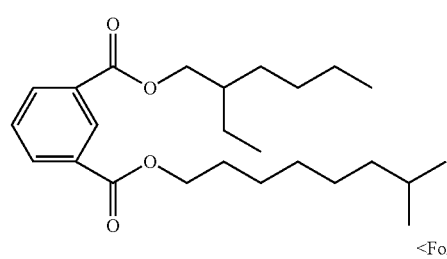

<Formula 1-17>

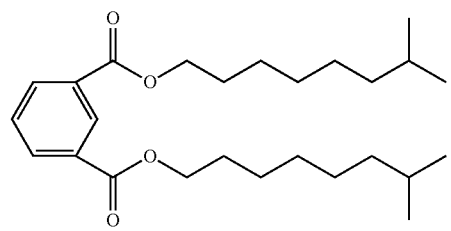

and

<Formula 1-20>

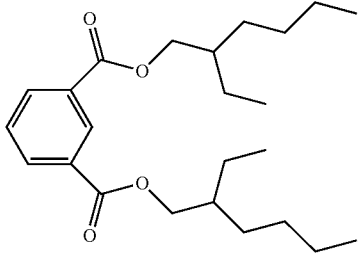

Hereinafter, the ester compound of the above Formula 1 according to an embodiment of the present invention or a preparation method of the plasticizer composition including the same will be explained in detail.

The ester compound or the plasticizer composition according to an embodiment of the present invention may be obtained by conducting an esterification reaction of isophthalic acid of the following Formula 2 with at least one alcohol of the following Formula 3 or a mixture of the alcohol with at least one isomer thereof in the presence of a catalyst.

<Formula 2>

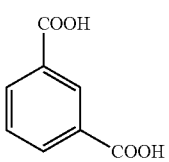

R'OH    <Formula 3>

In the above formula, R' is at least one selected from the group consisting of $C_3$-$C_{10}$ alkyl of a non-branch type or including at least one branched chain, a substituted or unsubstituted alkyl aryl and a substituted or unsubstituted aryl.

In this case, in the alcohol of the above Formula 3, the branched chain which may be included in R' may be $C_1$-$C_6$ alkyl, $C_2$-$C_6$ alkenyl or $C_2$-$C_6$ alkynyl.

The alcohol of the above Formula 2 according to an embodiment of the present invention may be an alcohol where R' includes one selected from the group consisting of $C_4$-$C_9$ alkyl of a non-branch type or including at least one $C_1$-$C_4$ alkyl branched chain, and phenyl or benzyl of a non-branch type or including at least one $C_1$-$C_4$ alkyl branched chain.

In the esterification reaction, an ester bond may be obtained by a dehydration condensation reaction of a carboxyl group (—COOH) substituted at a phenyl group in the isophthalic acid of Formula 2 with a hydroxyl group (OH) in at least 1 alcohol, preferably 1-3 alcohols.

The esterification reaction is preferably conducted at a temperature range of 80° C. to 270° C. for 1 to 15 hours. The reaction time may be counted after elevating the temperature of the reactant from the point reaching the reaction temperature.

When particularly examining, the isophthalic acid of the above Formula 2 and the alcohol of the above Formula 3 (or a mixture of the alcohol and at least one isomer thereof) may be used in a molar ratio of 1:0.01 to 5. In addition, according to another embodiment of the present invention, in the case of using at least two different alcohols as the alcohol of the above Formula 3, the molar ratio may be 1:0.1 to 4.9:0.1 to 4.9. For example, in the case that the isophthalic acid of the above Formula 2, 2-ethylhexanol (2-EH) as the alcohol of the above Formula 3 and 2-propylheptanol (2-PH) of the above Formula 6 (or a mixture of the 2-propylheptanol and at least one alcohol isomer thereof) are used according to an embodiment of the present invention, the molar ratio may be 1:0.1 to 4.9:0.1 to 4.9.

According to an embodiment of the present invention, the alcohol of the above Formula 3 may be prepared by a common method or used by purchasing a commercially available product. In the case of purchasing the commercially available product, the alcohol of the above Formula 3 may be included as a mixture with at least one alcohol isomer thereof, and the amount of the alcohol of the above Formula 3: the alcohol isomer thereof may be included in an amount ratio of, for example, 50 to 100 parts by weight: 0 to 50 parts by weight, and preferably, 70 to 100 parts by weight: 0 to 30 parts by weight.

For example, in the case that the alcohol of the above Formula 3 is 2-propylheptane-1-ol, 4-methyl-2-propylhexanol of the following Formula 3-1 or 5-methyl-2-propylhexanol of the following Formula 3-2 may be included as the isomer thereof.

<Formula 3-1>

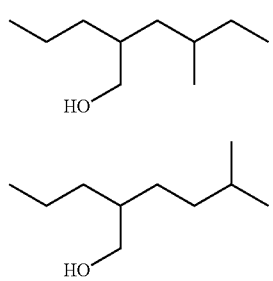

<Formula 3-2>

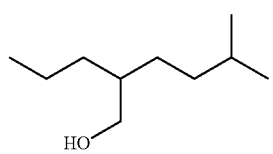

Further, as commercially available 2-propylheptane-1-ol, commercially available products of BASF Co., including the isomer thereof such as CAS No. 10042-59-8, 66256-62-0, 159848-27-8, etc. may be used, and as isononyl alcohol, commercially available products including the isomer thereof such as CAS No. 68526-84-1 of EXXONMOBILE Co., and CAS No. 27458-94-2 (68515-81-1) of KYOWA Co., etc. may be used. However, the present invention is not limited thereto.

In this case, if the molar ratio of the isophthalic acid and the alcohol is in the above range, an ester compound for a plasticizer having high purity, yield and process efficiency and excellent processability improving effects may be obtained.

The temperature of the esterification reaction after inserting raw materials and a catalyst may be elevated up to 270° C. and maintained for 1 to 15 hours, and unreacted alcohol evaporated during reaction may be condensed using a condenser and inserted again for continuous recycle. To effectively remove water generated during conducting the reaction, a nitrogen gas which is an inert gas may be directly inserted in the reactant until completing the reaction. Thus, a reaction product having an acid value of about 0.01 and conversion rate of 99% and over may be effectively obtained after completing the reaction.

After completing the reaction, a process of removing unreacted materials by maintaining for about 0.5 to 6 hours in vacuum conditions may be further included.

In addition, for removing a remaining unreacted acid, a cooling process, a neutralizing treatment by adding an appropriate amount of an aqueous alkaline solution and a washing process may be conducted. Then, water may be removed in vacuum for about 30 to 120 minutes until securing the water content to an appropriate degree and less. Finally, an appropriate amount of a filter medium is inserted, followed by stirring at about 80° C. to 110° C. for about 30 minutes and filtering to produce an isophthalate-based ester compound of the above Formula 1.

The catalyst inserted in the reaction may include a Sn-based or Ti-based organometallic catalyst, a sulfonic acid-based or sulfuric-based acid catalyst, or a mixture thereof.

The organometallic catalyst may include, for example, at least one selected from a titanium tetraalkoxide [Ti(OR)$_4$] such as tetraisobutyl titanate and tetraisopropyl titanate, a tin alkoxide [Sn(OR)$_2$] such as dibutyltin oxide, etc.

In addition, the acid catalyst may include, for example, at least one selected from paratoluenesulfonic acid, methanesulfonic acid, ethanesulfonic acid, propanesulfonic acid and sulfuric acid. The reaction catalyst may be included in an amount of 0.01 to 5.0 parts by weight with respect to 100 parts by weight of the isophthalic acid reaction material. In the case of using the catalyst less than the lower limit, reaction efficiency may be decreased, and in the case of exceeding the upper limit, a product may be discolored.

Further, the present invention may provide a plasticizer composition including the ester compound of the above Formula 1 and a polyvinyl chloride (PVC) resin composition including a polyvinyl chloride resin. In the PVC resin composition, the ester compound is added as a plasticizer.

The plasticizer composition may be included in an amount of 10 to 150 parts by weight with respect to 100 parts by weight of the polyvinyl chloride and may preferably be included in an amount of 20 to 100 parts by weight.

According to an embodiment of the present invention, in the amount range, hardness, tensile strength, elongation rate as well as processability with a resin such as short absorption rate and short melting time may be improved, and particularly, migration loss and volatile loss may be minimized.

In addition, the present invention may provide a resin composition including the plasticizer composition and a resin other than the PVC resin composition, and the resin may be a known resin in the art. For example, at least one selected from ethylenevinyl acetate, polyethylene, polypropylene, polystyrene, polyurethane, thermoplastic elastomer, polylactic acid, a synthetic rubber such as SBR, NBR, BR, etc. may be included, without limitation.

According to an embodiment of the present invention, the resin composition may further include a filler.

The filler may be 0 to 300 parts by weight, preferably, 50 to 200 parts by weight, and more preferably, 100 to 200 parts by weight on the basis of 100 parts by weight of the resin.

According to an embodiment of the present invention, the filler may be a known filler in this art, without specific limitation. For example, a mixture of at least one selected from silica, magnesium carbonate, calcium carbonate, hard charcoal, talc, magnesium hydroxide, titanium dioxide, magnesium oxide, calcium hydroxide, aluminum hydroxide, aluminum silicate, magnesium silicate and barium sulfate, may be used.

In addition, according to an embodiment of the present invention, the resin composition may further include other additives such as a stabilizer, as occasion demands.

Each of the other additives such as the stabilizer may be included in an amount of 0 to 20 parts by weight, and preferably 1 to 15 parts by weight on the basis of 100 parts by weight of the resin.

The stabilizer used according to an embodiment of the present invention may be Ca—Zn-based stabilizer such as a composite stearate of calcium-zinc, without specific limitation.

In addition, according to an embodiment of the present invention, the resin composition may further include at least one plasticizer composition selected from dioctyl terephthalate (DOTP), diisononyl phthalate (DINP), diisodecyl phthalate (DIDP), dipropylheptyl phthalate (DPHP), trioctyltrimellitate (TOTM), di-(2-ethylhexyl) terephthalate (DEHTP), dioctyl adipate (DOA), butyloctyl terephthalate (BOTP), dioctyl succinate (DOSx), neopentyl glycol-based, trimethylolpropane-based, diethylene glycol-based, triethylene glycol-based product. The amount of the plasticizer composition may be 0 to 150 parts by weight and preferably, 5 to 100 parts by weight on the basis of 100 parts by weight of the resin.

The resin composition has an absorption rate of the ester compound of 3 to 10 minutes, 3 to 8 minutes, and more preferably, 4 to 7 minutes. In the range, workability and processability are good.

The absorption rate may be evaluated by measuring a time period of mixing the resin and the ester compound using a mixer (Product name: Brabender, P600) until the torque of the mixer is stabilized under the conditions of 77° C. and 60 rpm.

The ester compound according to an embodiment of the present invention has short absorption rate and short melting time with respect to the resin, and the processability of the resin may be improved, and good physical properties may be provided when prescribing a sheet and a compound such as a cable, an interior material of a vehicle, a film, a sheet, a tube, a wall paper, a toy, a flooring material, etc.

Hereinafter, embodiments will be explained in detail to particularly explain the present invention. The present invention may, however, be embodied in different forms and should not be construed as limited to the embodiments set forth herein. Rather, these embodiments are provided so that this disclosure will be thorough and complete, and will fully convey the scope of the inventive concept to those skilled in the art.

EXAMPLES

Hereinafter, examples and experimental examples will be further explained, however the present invention is not limited to the following examples and experimental examples.

Example 1

To a four-necked, 3 liter reactor equipped with a cooler, a water stripper, a condenser, a decanter, a reflux pump, a temperature controller, a stirrer, etc., 498.0 g of purified isophthalic acid (PIA), 586 g of 2-ethylhexanol (2-EH), 721 g of 2-propylheptanol (2-PH, BASF Co.) (the molar ratio of PIA:2-EH:2-PH was 1.0:1.5:1.5) and 1.54 g of tetraisopropyl titanate (TIPT) as a titanium-based catalyst (0.31 parts by weight on the basis of 100 parts by weight of PIA) were inserted, followed by slowly elevating the temperature to about 170° C. The generation of water began at about 170° C. An esterification reaction was conducted at the reaction temperature of about 220° C. under an atmospheric pressure while continuously injecting a nitrogen gas for about 4.5 hours, and the reaction was terminated when an acid value reached 0.01.

After completing the reaction, a distillation extraction under a reduced pressure was conducted for 0.5 to 4 hours to remove unreacted raw materials. To remove the unreacted raw materials to a certain amount degree and less, steam extraction was conducted using steam under a reduced pressure for 0.5 to 3 hours. The reactant was cooled, and neutralization treatment was conducted using an alkaline solution. In addition, washing may be conducted, followed by dehydrating the reactant to remove water. A filter medium was inserted to the dehydrated reactant, followed by stirring for a certain time and filtering to obtain an isophthal-based plasticizer composition including 49 wt % of 2-ethylhexyl 2-propylheptyl isophthalate (EHPIP) of Formula 1-1, 17 wt % of di-(2-ethylhexyl) isophthalate (DEHIP) of Formula 1-20 and 34 wt % of di-(2-propylheptyl) isophthalate (DPIP) of Formula 1-21 (yield 99.0%).

Examples 2 to 13

In Examples 2 to 13, plasticizer compositions of the following Table 1 were obtained by applying the same conditions in Example 1 using the same molar ratio of the isophthalic acid and the alcohol while changing the kind of the alcohol.

Comparative Example 1

LGflex DPHP (trade name) of LG Chem. was used.

Comparative Example 2

Diisodecyl phthalate (DIDP; LGfex DIDP, LG Chem.) was used as a plasticizer.

Comparative Example 3

Diundecyl isophthalate was prepared by the same preparation method in Example 1 as a plasticizer.

Comparative Example 4

A plasticizer composition including 50 wt % of undecyl-isotridecyl isophthalate, 23 wt % of diundecyl isophthalate and 27 wt % of diisotridecyl isophthalate was prepared by conducting the same preparation method in Example 1.

TABLE 1

| | Ester-based composition (wt %) | | |
|---|---|---|---|
| Example 1 | Formula 1-1 (47%) | Formula 1-20 (17%) | Formula 1-21 (36%) |
| Example 2 | Formula 1-4 (53%) | Formula 1-16 (15%) | Formula 1-21 (32%) |
| Example 3 | Formula 1-5 (50%) | Formula 1-16 (20%) | Formula 1-17 (30%) |
| Example 4 | Formula 1-6 (48%) | Formula 1-16 (16%) | Formula 1-18 (36%) |
| Example 5 | Formula 1-7 (47%) | Formula 1-19 (35%) | Formula 1-16 (18%) |
| Example 6 | Formula 1-8 (44%) | Formula 1-20 (24%) | Formula 1-18 (32%) |
| Example 7 | Formula 1-9 (47%) | Formula 1-19 (28%) | Formula 1-20 (25%) |
| Example 8 | Formula 1-10 (49%) | Formula 1-21 (26%) | Formula 1-18 (25%) |
| Example 9 | Formula 1-11 (50%) | Formula 1-21 (30%) | Formula 1-19 (20%) |
| Example 10 | Formula 1-12 (47%) | Formula 1-17 (25%) | Formula 1-18 (38%) |
| Example 11 | Formula 1-13 (49%) | Formula 1-19 (19%) | Formula 1-17 (32%) |
| Example 12 | Formula 1-14 (46%) | Formula 1-19 (17%) | Formula 1-18 (37%) |
| Example 13 | Formula 1-15 (45%) | Formula 1-16 (21%) | Formula 1-20 (34%) |
| Comparative Example 1 | DPHP (100%) | | |
| Comparative Example 2 | DIDP (100%) | | |
| Comparative Example 3 | Diundecyl isophthalate (100%) | | |
| Comparative Example 4 | Undecyl, isotridecyl isophthalate (50%) | Diundecyl isophthalate (24%) | Diisotridecyl isophthalate (26%) |

<Manufacture of Specimen Using Polyvinyl Chloride Resin Composition (Sheet)>

Example 14

With respect to 100 parts by weight of polyvinyl chloride resin (PVC, LS 130 s), 50 parts by weight of an isophthal-based composition including 47 wt % of 2-ethylhexyl 2-propylheptyl isophthalate (EHPIP) of Formula 1-1, 17 wt % of di-(2-ethylhexyl) isophthalate (DEHIP) of Formula 1-20 and 36 wt % of di-(2-propylheptyl) isophthalate (DPIP) of Formula 1-prepared in Example 1, 5 parts by weight of a RUP stabilizer (RUP 144, Adeka Korea Co.) as an additive, 40 parts by weight of calcium carbonate (Omya 1 T, BSH) and 0.3 phr of stearic acid (ST/A) as a stabilizer were mixed and hand mixed. A process was conducted at 160° C. for 4 minutes using a roll mill, and at 180° C. for 2.5 minutes (low pressure) and for 2 minutes (high pressure) using a press to manufacture a sheet having a thickness of 1-3 mm.

Examples 15-26

Sheets were manufactured by conducting the same procedure described in Example 14 except for using the compositions of Examples 2 to 13 as a plasticizer.

Comparative Example 5

A sheet was manufactured by conducting the same procedure described in Example 14 except for using DPHP of Comparative Example 1 as a plasticizer.

Comparative Example 6

A sheet was manufactured by conducting the same procedure described in Example 14 except for using diisodecyl phthalate (DIDP; LGfex DIDP, LG Chem) of Comparative Example 2 as a plasticizer.

Comparative Example 7

A sheet was manufactured by conducting the same procedure described in Example 14 except for using diundecyl isophthalate of Comparative Example 3 as a plasticizer.

Comparative Example 8

A sheet was manufactured by conducting the same procedure described in Example 14 except for using 50 wt % of undecyl-isotridecyl isophthalate, 24 wt % of diundecyl isophthalate and 26 wt % of diisotridecyl isophthalate of Comparative Example 5 as a plasticizer.

Experimental Example 1: Evaluation of Physical Properties

Evaluation of performance with respect to hardness, tensile strength, elongation rate, migration loss, sheet volatile loss and plasticizer absorption rate were conducted for the sheets manufactured in Examples 14 to 26 and Comparative Examples 4 to 8. The results are shown in Table 2.

The conditions of each evaluation of performance are as follows.

Measuring Hardness

Shore hardness at 25° C., 3 T 10 s was measured using ASTM D2240.

Measuring Tensile Strength

By ASTM D638 method, a specimen was drawn in a cross head speed of 200 mm/min (1 T) using a test apparatus of U.T.M (manufacturer: Instron, model name: 4466), and a point where the specimen was cut was measured. The tensile strength was calculated as follows.

Tensile strength (kgf/cm$^2$)=load value (kgf)/thickness (cm)×width (cm)

Measuring Elongation Rate

By ASTM D638 method, a specimen was drawn in a cross head speed of 200 mm/min (1 T) using a test apparatus of U.T.M, and a point where the specimen was cut was measured. The elongation rate was calculated as follows.

Elongation rate (%)=length after elongation/initial length×100

Measuring Migration Loss

According to KSM-3156, a specimen with a thickness of 2 mm and over was obtained, PS plates were attached onto both sides of the specimen and a load of 1 kgf/cm$^2$ was applied. The specimen was stood in a hot air circulation type oven (80° C.) for 72 hours and then taken out and cooled at room temperature for 4 hours. Then, PS plates attached onto both sides of the specimen were removed, the weights before and after standing in the oven were measured, and the migration loss was calculated by the following equation.

Migration loss (%)={(initial weight of specimen at room temperature−weight of specimen after standing in oven)/initial weight of specimen at room temperature}×100

Measuring Sheet Volatile Loss

The specimen thus manufactured was processed at 100° C. for 168 hours, and the weight of the specimen was measured.

Volatile loss (wt %)=initial weight of specimen− (weight of specimen after processing at 100° C. for 168 hours)/initial weight of specimen×100

TABLE 2

| | Hardness (Shore "A") | Tensile strength (kg/cm$^2$) | Elongation rate (%) | Migration loss (%) | Volatile loss (%) |
|---|---|---|---|---|---|
| Example 14 | 90.7 | 183.4 | 227.8 | 0.11 | 2.09 |
| Example 15 | 87.6 | 181.5 | 285.1 | 0.48 | 2.35 |
| Example 16 | 86.7 | 179.5 | 282.6 | 0.56 | 3.20 |
| Example 17 | 88.5 | 182.6 | 286.9 | 0.39 | 1.02 |
| Example 18 | 87.2 | 175.6 | 259.4 | 0.55 | 0.88 |
| Example 19 | 93.5 | 195.6 | 288.6 | 0.08 | 0.85 |

TABLE 2-continued

| | Hardness (Shore "A") | Tensile strength (kg/cm$^2$) | Elongation rate (%) | Migration loss (%) | Volatile loss (%) |
|---|---|---|---|---|---|
| Example 20 | 91.4 | 194.7 | 268.9 | 0.10 | 0.90 |
| Example 21 | 93.3 | 207.9 | 291.5 | 0.03 | 0.35 |
| Example 22 | 90.3 | 201.7 | 268.5 | 0.15 | 0.55 |
| Example 23 | 92.5 | 208.5 | 284.6 | 0.05 | 0.30 |
| Example 24 | 91.4 | 201.3 | 251.3 | 0.14 | 0.56 |
| Example 25 | 91.5 | 204.6 | 260.5 | 0.15 | 0.48 |
| Example 26 | 87.6 | 182.4 | 232.5 | 0.14 | 2.53 |
| Comparative Example 6 | 89.5 | 185.6 | 231.7 | 0.89 | 1.89 |
| Comparative Example 7 | 90.0 | 183.5 | 241.2 | 0.18 | 1.07 |
| Comparative Example 8 | 92.2 | 210.3 | 221.5 | 0.04 | 0.35 |
| Comparative Example 9 | 93.8 | 214.9 | 216.5 | 0.02 | 0.25 |

The sheets of Examples 14 to 26 using the plasticizer compositions (Examples 1 to 13) according to an embodiment of the present invention as a plasticizer had appropriate physical properties for a resin and were secured to be used for an appropriate use. The isophthalates using an alcohol having a small molecular weight exhibited relatively good hardness and elongation property when compared to comparative examples, and the isophthalates using an alcohol having a large molecular weight exhibited the same or better physical properties of migration loss and volatile loss when compared to comparative examples. When the novel compound including the blended alcohol is appropriately applied according to use, good processing physical properties and physical effects satisfying required properties may be expected.

<Measuring Physical Properties of Plasticizer Compositions>

Examples 27 to 31

Example 27

To a four-necked, 3 liter reactor equipped with a cooler, a water stripper, a condenser, a decanter, a reflux pump, a temperature controller, a stirrer, etc., 498.0 g of purified isophthalic acid (PIA), 586 g of 2-ethylhexanol (2-EH), 721 g of 2-propylheptanol (2-PH, BASF Co. including 85-100 wt % of 2-PH, 0-15 wt % of 4-methyl-2-propyl-hexanol and 0-15 wt % of 5-methyl-2-propyl-hexanol) (the molar ratio of PIA:2-EH:2-PH was 1.0:1.5:1.5) and 1.24 g of tetra n-butyl titanate (TNBT) as a titanium-based catalyst (0.25 parts by weight on the basis of 100 parts by weight of PIA) were inserted, followed by slowly elevating the temperature to about 170° C. The generation of water began at about 170° C. An esterification reaction was conducted at the reaction temperature of about 220° C. under an atmospheric pressure while continuously injecting a nitrogen gas for about 3.5 hours, and the reaction was terminated when an acid value reached 0.3.

After completing the reaction, distillation extraction under a reduced pressure was conducted for 0.5 to hours to remove unreacted raw materials. To remove the unreacted raw materials to a certain amount degree and less, steam extraction was conducted using steam under a reduced pressure for 0.5 to 3 hours. The temperature of the reactant was lowered to about 90° C., and neutralization treatment was conducted using an alkaline solution. In addition, washing may be conducted, followed by dehydrating the reactant to remove water. A filter medium was inserted to the dehydrated reactant, followed by stirring for a certain time and filtering to obtain an isophthal-based plasticizer composition including 48 wt % of 2-ethylhexyl 2-propylheptyl isophthalate (EHPIP) of Formula 1, 17 wt % of di-(2-ethylhexyl) isophthalate (DEHIP) of Formula 2 and 35 wt % of di-(2-propylheptyl) isophthalate (DPIP) of Formula 3.

Example 28

To a four-necked, 3 liter reactor equipped with a cooler, a water stripper, a condenser, a decanter, a reflux pump, a temperature controller, a stirrer, etc., 498.0 g of purified isophthalic acid (PIA), 820 g of 2-ethylhexanol (2-EH, LG Chem.), 428 g of 2-propylheptanol (2-PH, BASF Co., including 85-100 wt % of 2-PH, 0-15 wt % of 4-methyl-2-propyl-hexanol and 0-15 wt % of 5-methyl-2-propyl-hexanol) (the molar ratio of PIA:2-EH:2-PH was 1.0:2.1:0.9) and 1.24 g of tetra n-butyl titanate (TNBT) as a titanium-based catalyst (0.25 parts by weight on the basis of 100 parts by weight of PIA) were inserted, followed by slowly elevating the temperature to about 170° C. The generation of water began at about 170° C. An esterification reaction was conducted at the reaction temperature of about 220° C. under an atmospheric pressure while continuously injecting a nitrogen gas for about 3 hours, and the reaction was terminated when an acid value reached 0.3.

After completing the reaction, a post-treatment such as removing of unreacted raw materials, neutralization, washing, dehydration, etc. was conducted as in Example 27. Finally, an isophthal-based plasticizer composition including 41 wt % of 2-ethylhexyl 2-propylheptyl isophthalate (EHPIP) of Formula 1, 46 wt % of di-(2-ethylhexyl) isophthalate (DEHIP) of Formula 2 and 13 wt % of di-(2-propylheptyl) isophthalate (DPIP) of Formula 3 was obtained.

Example 29

To a four-necked, 3 liter reactor equipped with a cooler, a water stripper, a condenser, a decanter, a reflux pump, a temperature controller, a stirrer, etc., 498.0 g of purified isophthalic acid (PIA), 1,055 g of 2-ethylhexanol (2-EH, LG Chem), 143 g of 2-propylheptanol (2-PH) (BASF Co., including 85-100 wt % of 2-PH, 0-15 wt % of 4-methyl-2-propyl-hexanol and 0-15 wt % of 5-methyl-2-propyl-hexanol) (the molar ratio of PIA:2-EH:2-PH was 1.0:2.7:0.3) and 1.24 g of tetra n-butyl titanate (TNBT) as a titanium-based catalyst (0.25 parts by weight on the basis of 100 parts by weight of PIA) were inserted, followed by slowly elevating the temperature to about 170° C. The generation of water began at about 170° C. An esterification reaction was conducted at the reaction temperature of about 220° C. under an atmospheric pressure while continuously injecting a nitrogen gas for about 3 hours, and the reaction was terminated when an acid value reached 0.3.

After completing the reaction, a post-treatment such as removing of unreacted raw materials, neutralization, washing, dehydration, etc. was conducted as in Example 27. Finally, an isophthal-based plasticizer composition including 77 wt % of 2-ethylhexyl 2-propylheptyl isophthalate (EHPIP) of Formula 1, 22 wt % of di-(2-ethylhexyl) isophthalate (DEHIP) of Formula 2 and 1 wt % of di-(2-propylheptyl) isophthalate (DPIP) of Formula 3 was obtained.

Example 30

To a four-necked, 3 liter reactor equipped with a cooler, a water stripper, a condenser, a decanter, a reflux pump, a temperature controller, a stirrer, etc., 498.0 g of purified isophthalic acid (PIA), 352 g of 2-ethylhexanol (2-EH, LG Chem), 997 g of 2-propylheptanol (2-PH) (BASF Co., including 85-100 wt % of 2-PH, 0-15 wt % of 4-methyl-2-propyl-hexanol and 0-15 wt % of 5-methyl-2-propyl-hexanol) (the molar ratio of PIA:2-EH:2-PH was 1.0:0.9:2.1) and 1.24 g of tetra n-butyl titanate (TNBT) as a titanium-based catalyst (0.25 parts by weight on the basis of 100 parts by weight of PIA) were inserted, followed by slowly elevating the temperature to about 170° C. The generation of water began at about 170° C. An esterification reaction was conducted at the reaction temperature of about 220° C. under an atmospheric pressure while continuously injecting a nitrogen gas for about 4 hours, and the reaction was terminated when an acid value reached 0.3.

After completing the reaction, a post-treatment such as removing of unreacted raw materials, neutralization, washing, dehydration, etc. was conducted as in Example 27. Finally, an isophthal-based plasticizer composition including 37 wt % of 2-ethylhexyl 2-propylheptyl isophthalate (EHPIP) of Formula 1, 6 wt % of di-(2-ethylhexyl) isophthalate (DEHIP) of Formula 2 and 57 wt % of di-(2-propylheptyl) isophthalate (DPIP) of Formula 3 was obtained.

Example 31

To a four-necked, 3 liter reactor equipped with a cooler, a water stripper, a condenser, a decanter, a reflux pump, a temperature controller, a stirrer, etc., 498.0 g of purified isophthalic acid (PIA), 117 g of 2-ethylhexanol (2-EH, LG Chem.), 1,287 g of 2-propylheptanol (2-PH) (BASF Co., including 85-100 wt % of 2-PH, 0-15 wt % of 4-methyl-2-propyl-hexanol and 0-15 wt % of 5-methyl-2-propyl-hexanol) (the molar ratio of PIA:2-EH:2-PH was 1.0:0.3:2.7) and 1.24 g of tetra n-butyl titanate (TNBT) as a titanium-based catalyst (0.25 parts by weight on the basis of 100 parts by weight of PIA) were inserted, followed by slowly elevating the temperature to about 170° C. The generation of water began at about 170° C. An esterification reaction was conducted at the reaction temperature of about 220° C. under an atmospheric pressure while continuously injecting a nitrogen gas for about 3 hours, and the reaction was terminated when an acid value reached 0.3.

After completing the reaction, a post-treatment such as removing of unreacted raw materials, neutralization, washing, dehydration, etc. was conducted as in Example 27. Finally, an isophthal-based plasticizer composition including 13.5 wt % of 2-ethylhexyl 2-propylheptyl isophthalate (EHPIP) of Formula 1, 0.5 wt % of di-(2-ethylhexyl) isophthalate (DEHIP) of Formula 2 and 86.0 wt % of di-(2-propylheptyl) isophthalate (DPIP) of Formula 3 was obtained.

Comparative Example 10

A phthalate-based plasticizer of diisodecyl phthalate (DIDP) of Exxonmobil was used.

<Manufacture of Specimen using Polyvinyl Chloride Resin Composition (Sheet)>

Examples 32 to 36 and Comparative Example 11

With respect to 100 parts by weight of polyvinyl chloride resin (PVC, LS 130 s), 50 parts by weight of the plasticizer compositions or compounds prepared in Examples 27 to 31 and Comparative Example 10, 5 parts by weight of a RUP stabilizer (RUP 144, Adeka Korea Co.) as an additive, 40 parts by weight of calcium carbonate (Omya 1 T, BSH) and 0.3 phr of stearic acid (ST/A) as a stabilizer were mixed. A process was conducted at 160° C. for 4 minutes using a roll mill, and at 180° C. for 2.5 minutes (low pressure) and for 2 minutes (high pressure) using a press to manufacture a sheet having a thickness of 1.3 mm. Sheets manufactured using the plasticizer compositions of Examples 27 to 31 were considered as Examples 32 to 46 one by one, and the sheet manufactured using the plasticizer composition of Comparative Example 10 was considered as Comparative Example 11.

Experimental Example 2: Evaluation of Physical Properties

Evaluation of performance on hardness, tensile strength, elongation rate, migration loss, sheet volatile loss and plasticizer absorption rate were conducted for the sheets manufactured in Examples 32 to 36 and Comparative Example 11. The results are shown in the following Table 3.

TABLE 3

|  | Example 32 | Example 33 | Example 34 | Example 35 | Example 36 | Comparative Example 11 |
| --- | --- | --- | --- | --- | --- | --- |
| Hardness (Shore "A") | 89.5 | 88.5 | 87.7 | 90.2 | 90.5 | 89.8 |
| Tensile strength (kgf/cm$^2$) | 196.8 | 193.9 | 191.9 | 190.2 | 187.0 | 171.5 |
| Elongation rate (%) | 302.8 | 303.0 | 309.1 | 300.1 | 300.1 | 282.6 |
| Migration loss (%) | 0.08 | 0.10 | 0.04 | 0.05 | 0.06 | 0.11 |
| Volatile loss (%) | 1.1 | 1.6 | 2.5 | 0.5 | 0.3 | 1.4 |

As shown in the above Table 3, when comparing the physical properties of the sheet of Comparative Example 11 obtained by using the plasticizer DIDP of Comparative Example 10 with those of the sheets of Examples 32 to 36 using the plasticizers of the examples of the present invention, the hardness in the examples was the same or better than that in Comparative Example 11, and the plasticizing efficiency of the plasticizers of Examples 27 to 31 is better than that of the plasticizer of Comparative Example 10. The tensile strength of the sheets of Examples 32 to 36 exhibited better efficiency than that of the sheet of Comparative Example 11, and the migration loss of the sheets of the examples was better three times than that of the sheet of Comparative Example 11.

Volatile loss of the sheets of Examples 35 to 36 was measured to decrease with good degree when compared to the sheet of Comparative Example 11 using the plasticizer of Comparative Example 10. The sheets of Examples 32 to 34 were secured to exhibit the same degree as the sheet of Comparative Example 11. As a result, the sheets of Examples 32 to 36 using the plasticizers of Examples 27 to 31 exhibited better physical properties than the sheet of Comparative Example 11 using a common plasticizer of Comparative Example 10.

Examples 37 to 40

Example 37

To a four-necked, 3 liter reactor equipped with a cooler, a water stripper, a condenser, a decanter, a reflux pump, a temperature controller, a stirrer, etc., 498.0 g of purified isophthalic acid (PIA), 712.5 g of 2-propylheptanol (2-PH) (BASF Co., including 85-100 wt % of 2-PH, 0-15 wt % of 4-methyl-2-propyl-hexanol and 0-15 wt % of 5-methyl-2-propyl-hexanol) and 649.4 g of isononyl alcohol (INA) (the molar ratio of PIA:2-PH:INA was 1.0:1.5:1.5) and 1.54 g of tetra isopropyl titanate (TIPT) as a titanium-based catalyst (0.31 parts by weight on the basis of 100 parts by weight of PIA) were inserted, followed by slowly elevating the temperature to about 170° C. The generation of water began at about 170° C. An esterification reaction was conducted at the reaction temperature of about 220° C. under an atmospheric pressure while continuously injecting a nitrogen gas for about 4.5 hours, and the reaction was terminated when an acid value reached 0.01.

After completing the reaction, unreacted alcohol in the reactant was removed by distillation, and the reactant was neutralized/washed, and filtered to finally produce an isophthal-based plasticizer composition including 42 wt % of 2-propylhepty isononyl isophthalate (PINIP) of Formula 1, 31 wt % of di-(2-propylheptyl) isophthalate (DPIP) of Formula 2 and 27 wt % of diisononyl isophthalate (DINIP) of Formula 3.

Example 38

An isophthal-based plasticizer composition including wt % of 2-propylhepty isononyl isophthalate (PINIP) of Formula 1, 21 wt % of di-(2-propylheptyl) isophthalate (DPIP) of Formula 2 and 37 wt % of diisononyl isophthalate (DINIP) of Formula 3 was finally obtained by conducting the same procedure described in Example 37 except for using, as the alcohol, 427.4 g of 2-propylheptanol (2-PH) (BASF Co., including 85-100 wt % of 2-PH, 0-15 wt % of 4-methyl-2-propyl-hexanol and 0-15 wt % of 5-methyl-2-propyl-hexanol) and 909.1 g of isononyl alcohol (INA) (the molar ratio of PIA:2-PH:INA was 1.0:0.9:2.1) and filtering.

Example 39

An isophthal-based plasticizer composition including 23 wt % of 2-propylhepty isononyl isophthalate (PINIP) of Formula 1, 10 wt % of di-2-propylheptyl isophthalate (DPIP) of Formula 2 and 67 wt % of diisononyl isophthalate (DINIP) of Formula 3 was finally obtained by conducting the same procedure described in Example 37 except for using, as the alcohol, 142.5 g of 2-propylheptanol (2-PH) (BASF Co., including 85-100 wt % of 2-PH, 0-15 wt % of 4-methyl-2-propyl-hexanol and 0-15 wt % of 5-methyl-2- propyl-hexanol) and 1,168.8 g of isonyl alcohol (INA) (the molar ratio of PIA:2-PH:INA was 1.0:0.3:2.7) and filtering.

Example 40

An isophthal-based plasticizer composition including wt % of 2-propylhepty isononyl isophthalate (PINIP) of Formula 1, 55 wt % of di-2-propylheptyl isophthalate (DPIP) of Formula 2 and 8 wt % of diisononyl isophthalate (DINIP) of Formula 3 was finally obtained by conducting the same procedure described in Example 37 except for using, as the alcohol, 997.3 g of 2-propylheptanol (2-PH) (BASF Co., including 85-100 wt % of 2-PH, 0-15 wt % of 4-methyl-2-propyl-hexanol and 0-15 wt % of 5-methyl-2-propyl-hexanol) and 389.6 g of isononyl alcohol (INA) (the molar ratio of PIA:2-PH:INA was 1.0:2.1:0.9) and filtering.

Comparative Example 12

A phthalate-based plasticizer of diisodecyl phthalate (DIDP) of Exxonmobil was used.

<Manufacture of Specimen Using Polyvinyl Chloride Resin Composition (Sheet)>

Examples 41 to 44 and Comparative Example 13

With respect to 100 parts by weight of polyvinyl chloride resin (PVC, LS 130 s), 50 parts by weight of the plasticizer compositions or compounds prepared in Examples 37 to 40 and Comparative Example 12, 5 parts by weight of a RUP stabilizer (RUP 144, Adeka Korea Co.) as an additive, 40 parts by weight of calcium carbonate (Omya 1 T, BSH) and 0.3 phr of stearic acid (ST/A) as a stabilizer were mixed. A process was conducted at 160° C. for 4 minutes using a roll mill, and at 180° C. for 2.5 minutes (low pressure) and for 2 minutes (high pressure) using a press to manufacture a sheet having a thickness of 1 mm and 3 mm. Sheets manufactured using the plasticizer compositions of Examples 37 to 40 were considered as Examples 41 to 44 one by one, and the sheet manufactured using the plasticizer composition of Comparative Example 12 was considered as Comparative Example 13.

Experimental Example 3: Evaluation of Physical Properties

Evaluation of performance on hardness, tensile strength, elongation rate, migration loss, sheet volatile loss and plasticizer absorption rate were conducted for the sheets manufactured in Examples 41 to 44 and Comparative Example 13. The results are shown in the following Table 4.

TABLE 4

|  | Example 41 | Example 42 | Example 43 | Example 44 | Comparative Example 13 |
| --- | --- | --- | --- | --- | --- |
| Hardness (Shore "A") | 91 | 91.5 | 90 | 91.5 | 91 |
| Tensile strength (kgf/cm$^2$) | 194.1 | 189.4 | 173.8 | 198.9 | 193.3 |
| Elongation rate (%) | 293.8 | 295.2 | 289.8 | 300.2 | 278.2 |
| Migration loss (%) | 0.04 | 0.08 | 0.07 | 0.02 | 0.10 |

TABLE 4-continued

|  | Example 41 | Example 42 | Example 43 | Example 44 | Comparative Example 13 |
| --- | --- | --- | --- | --- | --- |
| Volatile loss (%) | 1.03 | 1.06 | 1.08 | 0.97 | 1.2 |

As shown in the above Table 4, when comparing the physical properties of the sheet of Comparative Example 13 obtained by using the plasticizer DIDP of Comparative Example 12 with those of the sheets of Examples 41 to 44 using the plasticizers of the examples of the present invention, the hardness in the examples was the same or better than that in Comparative Example 13, and the plasticizing efficiency of the plasticizers of the examples is better than a common product.

The tensile strength of the sheets of Examples 41 to 44 exhibited the same or better efficiency than that of the sheet of Comparative Example 13, and the migration loss in Examples 41 to 44 was better up to five times than in Comparative Example 13.

Volatile loss of the sheets of Examples 41 to 44 was secured to decrease with good degree when compared to the sheet of Comparative Example 13 using the plasticizer of Comparative Example 12.

As a result, the sheets of Examples 41 to 44 using the plasticizers of Examples 37 to 40 exhibited better physical properties than the sheet of Comparative Example 13 using a common plasticizer of Comparative Example 12.

Examples 45 to 49

Example 45

To a four-necked, 3 liter reactor equipped with a cooler, a water stripper, a condenser, a decanter, a reflux pump, a temperature controller, a stirrer, etc., 498.0 g of purified isophthalic acid (PIA), 117.2 g of 2-ethylhexanol (2-EH), 1,168.4 g of isononyl alcohol (INA) (the molar ratio of PIA:2-EH:INA was 1.0:0.3:2.7) and 1.54 g of tetra isopropyl titanate (TIPT) as a titanium-based catalyst (0.31 parts by weight on the basis of 100 parts by weight of PIA) were inserted, followed by slowly elevating the temperature to about 170° C. The generation of water began at about 170° C. An esterification reaction was conducted at the reaction temperature of about 220° C. under an atmospheric pressure while continuously injecting a nitrogen gas for about 4.5 hours, and the reaction was terminated when an acid value reached 0.2.

After completing the reaction, distillation-extraction under a reduced pressure was conducted for 0.5 to 4 hours to remove unreacted raw materials. To remove the unreacted raw materials to a certain amount degree and less, steam extraction was conducted using steam under a reduced pressure for 0.5 to 3 hours. The temperature of the reactant was lowered to about 90° C., and neutralization treatment was conducted using an alkaline solution. In addition, washing may be conducted, followed by dehydrating the reactant to remove water. A filter medium was inserted to the dehydrated reactant, followed by stirring for a certain time and filtering to obtain an isophthal-based plasticizer composition including 16 wt % of 2-ethylhexyl isononyl isophthalate (EHINIP) of Formula 1, 1 wt % of di-(2-ethylhexyl) isophthalate (DEHIP) of Formula 2 and 83 wt % of di-isononyl isophthalate (DINIP) of Formula 3.

Example 46

An isophthal-based plasticizer composition including wt % of 2-ethylhexyl isononyl isophthalate (EHINIP) of Formula 1, 7 wt % of di-(2-ethylhexyl) isophthalate (DEHIP) of Formula 2 and 49 wt % of diisononyl isophthalate (DINIP) of Formula 3 was finally obtained by conducting the same procedure described in Example 45 except for using, as the alcohol, 351.6 g of 2-ethylhexanol (2-EH) and 908.8 g of isononyl alcohol (INA) (the molar ratio of PIA:2-PH:INA was 1.0:0.9:2.1) and filtering.

Example 47

An isophthal-based plasticizer composition including wt % of 2-ethylhexyl isononyl isophthalate (EHINIP) of Formula 1, 20 wt % of di-(2-ethylhexyl) isophthalate (DEHIP) of Formula 2 and 25 wt % of diisononyl isophthalate (DINIP) of Formula 3 was finally obtained by conducting the same procedure described in Example 45 except for using, as the alcohol, 586.0 g of 2-ethylhexanol and 649.1 g of isononyl alcohol (INA) (the molar ratio of PIA:2-PH:INA was 1.0:1.5:1.5) and filtering.

Example 48

An isophthal-based plasticizer composition including 46 wt % of 2-ethylhexyl isononyl isophthalate (EHINIP) of Formula 1, 44 wt % of di-(2-ethylhexyl) isophthalate (DEHIP) of Formula 2 and 10 wt % of diisononyl isophthalate (DINIP) of Formula 3 was finally obtained by conducting the same procedure described in Example 45 except for using, as the alcohol, 820.5 g of 2-ethylhexanol and 389.5 g of isononyl alcohol (INA) (the molar ratio of PIA:2-PH:INA was 1.0:2.1:0.9) and filtering.

Example 49

An isophthal-based plasticizer composition including 20 wt % of 2-ethylhexyl isononyl isophthalate (EHINIP) of Formula 1, 79 wt % of di-(2-ethylhexyl) isophthalate (DEHIP) of Formula 2 and 1 wt % of diisononyl isophthalate (DINIP) of Formula 3 was finally obtained by conducting the same procedure described in Example 45 except for using, as the alcohol, 1,054.9 g of 2-ethylhexanol (2-EH) and 129.8 g of isononyl alcohol (INA) (the molar ratio of PIA:2-PH:INA was 1.0:2.7:0.3) and filtering.

Comparative Example 14

A phthalate-based plasticizer of diisodecyl phthalate (DIDP) of Exxonmobil was used.

<Manufacture of Specimen Using Polyvinyl Chloride Resin Composition (Sheet)>

Examples 50 to 54 and Comparative Example 15

With respect to 100 parts by weight of polyvinyl chloride resin (PVC, LS 100 s), 50 parts by weight of the plasticizer compositions or compounds prepared in Examples 45 to 49 and Comparative Example 14, 5 parts by weight of a RUP stabilizer (RUP 144, Adeka Korea Co.) as an additive, 40 parts by weight of calcium carbonate (Omya 1 T, BSH) and 0.3 phr of stearic acid (ST/A) as a stabilizer were mixed. The mixing was conducted using a 3 L super mixer (Korea EM) at 200 rpm for 2 minutes and at 500 rpm for 3 minutes, and the mixing was conducted while increasing to 700 rpm to 100° C. to produce a final mixture. A process was conducted at 160° C. for 4 minutes using a roll mill, and at 180° C. for 2.5 minutes (low pressure) and for 2 minutes (high pressure) using a press to manufacture a sheet having a thickness of 1 mm and 3 mm. Sheets thus manufactured were considered as Examples 50 to 54 and Comparative Example 15.

Experimental Example 4: Evaluation of Physical Properties

Performance evaluation on hardness, tensile strength, elongation rate, migration loss, sheet volatile loss and plasticizer absorption rate were conducted for the sheets manufactured in Examples 50 to 54 and Comparative Example 15. The results are shown in the following Table 5.

TABLE 5

| (2-EH:INA) | Example 50 (1:9) | Example 51 (3:7) | Example 52 (5:5) | Example 53 (7:3) | Example 54 (9:1) | Comparative Example 15 |
|---|---|---|---|---|---|---|
| Hardness (Shore "A") | 89.2 | 88.7 | 88.5 | 88.0 | 87.7 | 90.0 |
| Tensile strength (kgf/cm$^2$) | 188.7 | 189.9 | 194.2 | 192.5 | 190.2 | 183.5 |
| Elongation rate (%) | 298.2 | 294.9 | 297.0 | 303.5 | 295.5 | 281.2 |
| Migration loss (%) | 0.12 | 0.12 | 0.14 | 0.15 | 0.17 | 0.18 |
| Volatile loss (%) | 1.03 | 1.34 | 1.97 | 2.40 | 2.70 | 1.07 |

2-EH:INA represents the molar ratio of 2-ethylhexyl alcohol (2-EH):isononyl alcohol (INA) added during preparing a plasticizer.

As shown in the above Table 5, it could be secured that the sheets of Examples 50 to 54 using the plasticizers of Examples 45 to 49 of the present invention have lower hardness than the sheet of Comparative Example 15 obtained by using the plasticizer of Comparative Example 11.

When examining the difference of physical properties according to the molar ratio of 2-EH:INA of the sheets of Examples 50 to 54, plasticizing efficiency was increased when the ratio of 2-EH was increased during preparing the plasticizer. In addition, it could be secured that the migration loss was improved according to the increase of the ratio of INA during preparing the plasticizer.

The tensile strength and the elongation rate of the sheets of Examples 50 to 54 was somewhat higher and exhibited similar degree without great difference when compared to the sheet of Comparative Example 15.

The migration loss of the sheets of Examples 50 to 54 were good when compared to that of Comparative Example 15, and as a result, it could be secured that good physical properties were exhibited in the sheets of Examples 50 to 54 using the plasticizers of Examples 45 to 49 when compared to that of Comparative Example 15 using a common plasticizer of Comparative Example 14.

The invention claimed is:

1. A plasticizer composition comprising:
an ester compound represented by Formula 1:

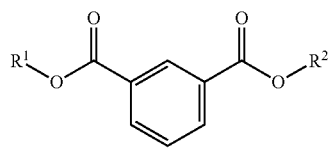
<Formula 1> in the above formula, $R^1$ and $R^2$ are different from each other and are independently at least one selected from the group consisting of $C_3$-$C_{10}$ alkyl of a non-branch type or including at least one branched chain, a substituted or unsubstituted alkyl aryl and a substituted or unsubstituted aryl; and at least two compounds selected from the group consisting of compounds represented by Formulas 1-16 to 1-21:

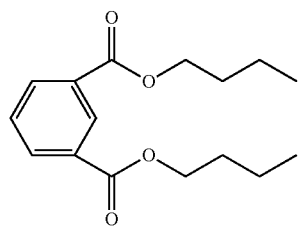
<Formula 1-16>

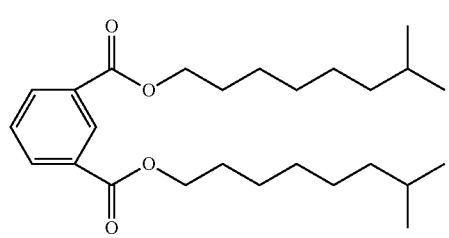
<Formula 1-17>

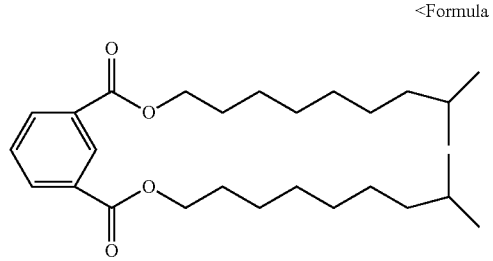
<Formula 1-18>

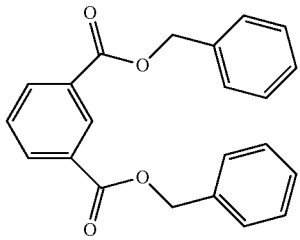
<Formula 1-19>

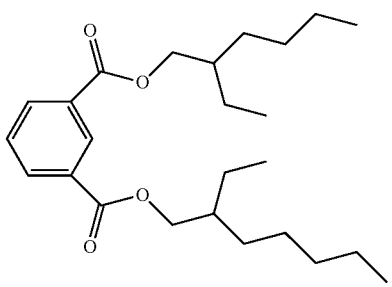
<Formula 1-20>

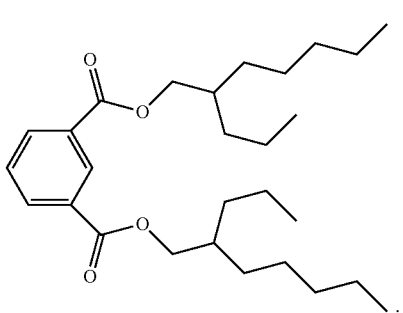
<Formula 1-21>

2. The plasticizer composition of claim 1, wherein the plasticizer composition comprises compounds of the following formulae:

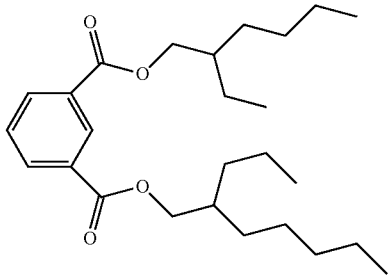
<Formula 1-1>

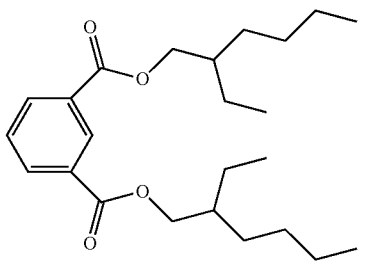
<Formula 1-20>

-continued

<Formula 1-21>

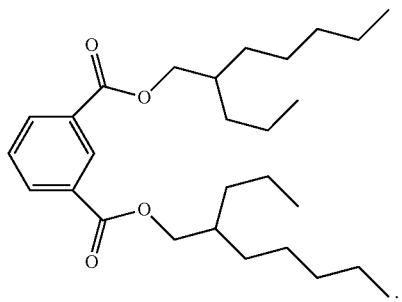

3. The plasticizer composition of claim 1, wherein the plasticizer composition comprises compounds of the following formulae:

<Formula 1-2>

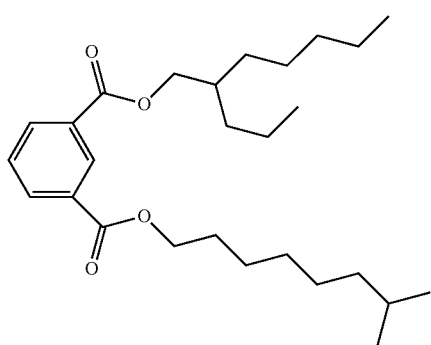

<Formula 1-17>

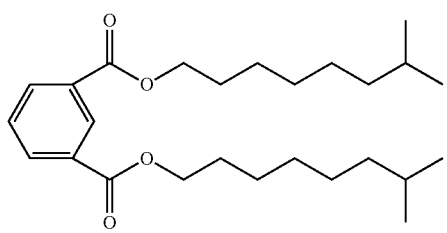

<Formula 1-21>

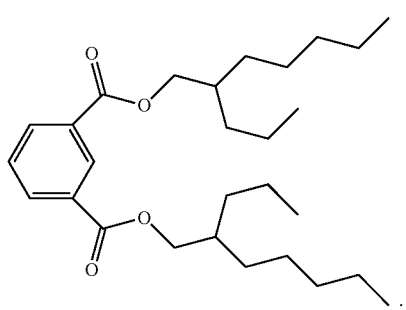

4. The plasticizer composition of claim 1, wherein the plasticizer composition comprises compounds of the following formulae:

<Formula 1-3>

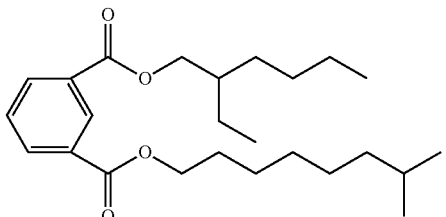

<Formula 1-17>

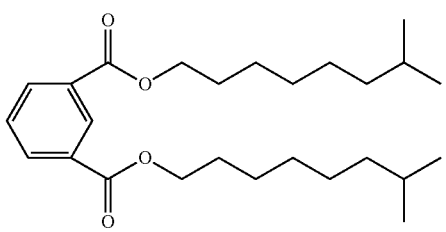

<Formula 1-20>

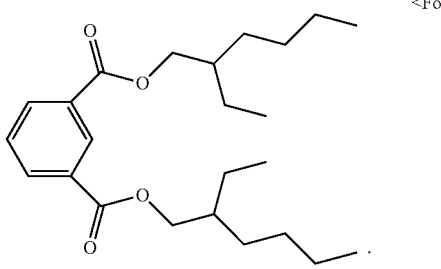

5. A polyvinyl chloride resin composition comprising the plasticizer composition of claim 1 and a polyvinyl chloride resin.

6. The polyvinyl chloride resin composition of claim 5, wherein the plasticizer composition is comprised in an amount of 10 to 150 parts by weight on the basis of 100 parts by weight of the polyvinyl chloride resin.

7. A resin composition comprising the plasticizer composition of claim 1 and a resin.

8. The resin composition of claim 7, wherein the resin comprises at least one selected from ethylenevinyl acetate, polyethylene, polypropylene, polystyrene, polyurethane, thermoplastic elastomer, polylactic acid, SBR, NBR and BR.

9. The resin composition of claim 7, wherein the plasticizer composition is comprised in an amount of 10 to 150 parts by weight on the basis of 100 parts by weight of the resin.

* * * * *